(12) United States Patent
Højlund Nielsen et al.

(10) Patent No.: US 11,760,718 B2
(45) Date of Patent: Sep. 19, 2023

(54) PRODUCTION OF ACETONITRILE AND/OR HYDROGEN CYANIDE FROM AMMONIA AND METHANOL

(71) Applicant: HALDOR TOPSØE A/S, Kgs. Lyngby (DK)

(72) Inventors: Poul Erik Højlund Nielsen, Fredensborg (DK); Rasmus Munksgård Nielsen, Måløv (DK); Brian Kjærgaard Olsen, Copenhagen S (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 12 days.

(21) Appl. No.: 16/469,841

(22) PCT Filed: Feb. 1, 2018

(86) PCT No.: PCT/EP2018/052471
§ 371 (c)(1),
(2) Date: Jun. 14, 2019

(87) PCT Pub. No.: WO2018/141826
PCT Pub. Date: Aug. 9, 2018

(65) Prior Publication Data
US 2020/0095193 A1    Mar. 26, 2020

(30) Foreign Application Priority Data
Feb. 6, 2017 (DK) .......................... PA 2017 00071

(51) Int. Cl.
*C07C 253/16* (2006.01)
*B01J 21/04* (2006.01)
*B01J 23/835* (2006.01)
*C01C 3/02* (2006.01)

(52) U.S. Cl.
CPC ............. *C07C 253/16* (2013.01); *B01J 21/04* (2013.01); *B01J 23/835* (2013.01); *C01C 3/0241* (2013.01)

(58) Field of Classification Search
CPC ....... C07C 253/16; B01J 21/04; B01J 23/835; B01J 27/22; B01J 35/002; B01J 23/80; C01C 3/0241
See application file for complete search history.

(56) References Cited

U.S. PATENT DOCUMENTS 2,337,421 A    12/1943  Spence et al.
2,337,422 A    12/1943  Spence et al.
(Continued)

FOREIGN PATENT DOCUMENTS

CN    104275190 A    1/2015
EP    0107638 A2    5/1984
(Continued)

OTHER PUBLICATIONS

International Search Report and Written Opinion issued in corresponding International Patent Application No. PCT/EP2018/052471, 10 pages (dated Mar. 28, 2018).
Search Report issued in corresponding Danish Patent Application No. PA 2017 00071, 8 pages (dated July 4, 2017).

*Primary Examiner* — Anthony J Zimmer
*Assistant Examiner* — Jordan W Taylor
(74) *Attorney, Agent, or Firm* — Boone IP Law (57) ABSTRACT

The invention relates to a process for producing a product gas comprising acetonitrile and/or hydrogen cyanide from a feed stream comprising ammonia and methanol over a solid catalyst comprising a support, a first metal and a second metal on the support, wherein the first metal and the second metal are in the form of a chemical compound, wherein the first metal is Fe, Ru or Co and the second metal is Sn, Zn, or Ge. The pressure is ambient pressure or higher and the (Continued)

temperature lies in a range from about 400° C. to about 700° C. Thus, the process for producing acetonitrile and/or hydrogen cyanide from ammonia and methanol may be catalyzed by a single catalyst and may be carried out in a single reactor. The invention also relates to a catalyst, a method for activating a catalyst and use of a catalyst for catalysing production of acetonitrile and/or hydrogen cyanide from ammonia and methanol.

7 Claims, 1 Drawing Sheet

(56) References Cited

U.S. PATENT DOCUMENTS

| 3,911,089 | A | * | 10/1975 | Shiraishi | B01J 23/8875 423/376 |
|---|---|---|---|---|---|
| 6,204,407 | B1 | | 3/2001 | Godbole et al. | |
| 2008/0317656 | A1 | | 12/2008 | Koryabkina et al. | |

FOREIGN PATENT DOCUMENTS

| EP | 0322796 A1 | * | 7/1989 | B01J 37/04 |
|---|---|---|---|---|
| FR | 2735770 A1 | | 12/1996 | |
| WO | 02070465 A1 | | 9/2002 | |
| WO | 2011088616 A1 | | 7/2011 | |
| WO | 2016062551 A1 | | 4/2016 | |

* cited by examiner

PRODUCTION OF ACETONITRILE AND/OR HYDROGEN CYANIDE FROM AMMONIA AND METHANOL

FIELD OF THE INVENTION

Embodiments of the invention generally relate to a process for producing a product gas comprising acetonitrile and/or hydrogen cyanide from a feed stream comprising ammonia and methanol over a catalyst, a catalyst for catalysing reactions producing a product gas comprising acetonitrile and/or hydrogen cyanide from a feed stream comprising ammonia and methanol, a method for activating a catalyst and use of a catalyst for catalysing reactions producing a product gas comprising acetonitrile and/or hydrogen cyanide from a feed stream comprising ammonia and methanol.

BACKGROUND

Aliphatic nitriles are important starting materials for polymers as well as for the synthesis of e.g., pharmaceuticals and pesticides. The carbon—nitrogen bond is extremely polar, which results in nitriles having a high dipole moment. Nitriles are good solvents for both polar and nonpolar solutes.

Nitriles may be produced by reaction of nitrogen-free precursors (such as alkanes, olefins, alcohols, aldehydes, or acids) with ammonia. Gas phase reaction of olefins with ammonia in the presence of oxygen (ammoxidation) and oxidation catalysts has attained the greatest industrial importance for the production of acrylonitrile from propene and methacrylonitrile from isobutene. This process is known as the Sohio process. An alternative process to produce nitriles is the reaction of hydrogen cyanide or cyanide ions with double bonds, carbonyl compounds, hydrogen or halogens (see Ullmann's Encyclopedia of Industrial Chemistry, Published Online: 15 Jun. 2000).

Hydrogen cyanide forms in at least limited amounts from many combinations of hydrogen, carbon, and ammonia. Hydrogen cyanide is currently produced in great quantities by several processes, as well as being a recovered waste product from the manufacture of acrylonitrile. An important process is the Andrussow oxidation invented by Leonid Andrussow in which methane and ammonia react in the presence of oxygen at about 1200° C. over a platinum catalyst.

U.S. Pat. No. 2,337,421 describes preparing aliphatic or arylaliphatic nitriles from alcohols of at least two carbon atoms by passing a mixture of ammonia and the vapors of the alcohols over a catalyst comprising reduced silver, and U.S. Pat. No. 2,337,422 describes preparation of nitriles a primary aliphatic alcohol of at least two carbon atoms over a catalyst of reduced copper.

It is an object of the invention to provide a process and a catalyst for catalysing the production of a product gas comprising acetonitrile and/or hydrogen cyanide from ammonia and methanol. It is also an object of the invention to provide a process and a catalyst for catalysing the production of acetonitrile and/or hydrogen cyanide from methanol and ammonia with a high selectivity and/or conversion. Another object of the invention is to provide a process and catalyst for forming a $C_2$ species from a $C_1$ species.

SUMMARY OF THE INVENTION

One embodiment of the invention provides a process for producing a product gas comprising acetonitrile and/or hydrogen cyanide from a feed stream comprising ammonia and methanol over a solid catalyst, where the catalyst comprises a support, a first metal and a second metal on the support, wherein the first metal and the second metal are in the form of a chemical compound, wherein the first metal is Fe, Ru or Co, and the second metal is Sn, Zn, or Ge, and wherein the pressure is ambient pressure or higher and the temperature lies in a range from about 400° C. to about 700° C. It has been shown that this catalyst is well suited to catalyse the appropriate reactions from methanol and ammonia to acetonitrile and/or hydrogen cyanide. Thus, the necessary sub-reactions of the process for producing acetonitrile and/or hydrogen cyanide from a feed stream comprising ammonia and methanol may be catalyzed by a single catalyst and may be carried out in a single reactor comprising the catalyst.

In an embodiment, the temperature lies in a range from about 500° C. to about 600° C. This is advantages in that it ensures sufficient production of hydrogen cyanide, being part of the reactions forming acetonitrile from ammonia and methanol.

In an embodiment, the catalyst comprises alloys between the first and second metals and/or ternary carbides comprising the first and the second metals.

In an embodiment, the support of the catalyst is chosen between the following: alumina, a spinel of alumina, a high temperature stable catalyst carrier in the form of an oxide a carbide or a nitride. As an example, the spinel of alumina may be $ZnAl_2O_4$ or $MgAl_2O_4$, and the oxide could e.g. be $CeO_2$ or $ZrO_2$.

In an embodiment, the catalyst is arranged to catalyse the following reactions:

1a) Amination of methanol to methylamine,
1b) Dehydrogenation of methylamine to hydrogen cyanide, and
2) Cyanation of methanol to acetonitrile.

The amination of methanol to methylamine follows the reaction:

$$CH_3OH+NH_3 \rightarrow CH_3NH_2+H_2O, \text{ having } (CH_3)_2NH, (CH_3)_3N \text{ as byproducts.} \tag{1a}$$

The dehydrogenation of methylamine follows the reaction:

$$CH_3NH_2 \rightarrow HCN+2H_2. \tag{1b}$$

The cyanation of methanol follows the reaction:

$$CH_3OH+HCN \rightarrow CH_3CN+H_2O. \tag{2}$$

In total, acetonitrile can be synthesized from methanol, MeOH, and ammonia. The formation of acetonitrile provides for a chemical platform for a range of products. For example, acetonitrile and methanol provides for synthesis of acrylonitrile: (3) $CH_3OH+CH_3CN \rightarrow CH_2CHCN+H_2+H_2O$. This is advantageous in that direct synthesis of acrylonitrile from propane requires high temperatures, above 600° C., encompassing risk of thermal cracking of propane. Other examples include forming acetic acid by hydrolyzing acetonitrile or hydrogenating acetonitrile to form ethylamine.

In an embodiment, the ratio between acetonitrile and hydrogen cyanide in the product gas is controlled by controlling the ratio of ammonia and methanol in the feed stream and/or the process temperature. In this embodiment, not all the hydrogen cyanide is used for cyanation of methanol. The ratio between acetonitrile and hydrogen cyanide in the product gas may e.g. be such that the product gas comprises acetonitrile and no hydrogen cyanide. Alternatively, the product gas may comprise hydrogen cyanide, but no acetonitrile. Moreover, any appropriate ratio between acetonitrile and hydrogen cyanide in the product gas is conceivable.

Another aspect of the invention relates to a catalyst for catalysing reactions producing a product gas comprising acetonitrile and/or hydrogen cyanide from a feed stream comprising ammonia and methanol, the catalyst comprising a support, a first metal and a second metal on the support, wherein the first metal and the second metal are in the form of a chemical compound, where the first metal is Fe, Ru or Co, and where the second metal is Sn, Zn or Ge, wherein the catalyst comprises alloys between the first and second metals and/or ternary carbides comprising the first metal and the second metal. It has been shown that this catalyst is well suited to catalyse the amination of methanol, a subsequent dehydrogenation of methylamine and a cyanidation reaction of methanol to acetonitrile and steam. Typically, the alloys between the first and second metals are present on the surface of the catalyst. This catalyst is a catalyst that has been active from its non-activated form, so that the catalyst comprises alloys between the first and second metals and/or ternary carbides comprising the first metal and the second metal; such alloys and/or carbides are not present in the non-activated catalyst.

In an embodiment, the catalyst is an activated catalyst that has been transformed from a non-activated catalyst by passing a feed stream comprising ammonia and methanol over the non-activated catalyst for at least 1 hour at a temperature of between about 400° C. and about 700° C. at a space velocity of at least 1000 $h^{-1}$. For example, the reactant gas stream comprises 10 vol % $CH_3OH$ and 9 vol % $NH_3$ in $N_2$, the space velocity is 8000 $h^{-1}$, the temperature is 400° C. or 500° C. and the activation time is 1 hour or 2 hours. Before activation, no alloys between the first and second metals or ternary carbides comprising the first and second metals exist on the catalyst. These are formed during the activation.

A step prior to activation of the catalyst by use of a feed stream comprising ammonia and methanol is a reduction of the catalyst. This may e.g. be carried out by passing 10 vol % $H_2$ in $N_2$ over a non-reduced (and non-activated) catalyst for 4 hours at a space velocity of 16000 $h^{-1}$ at a temperature of between about 500° C. and about 800° C.

In an embodiment, the non-activated catalyst comprises a support, a first metal and a second metal on the support, wherein the first metal and the second metal are in the form of a chemical compound, where the first metal is Fe, Ru Co, and where the second metal is Sn, Zn or Ge. The difference between the non-activated and the activated catalyst is at least that the activated catalyst comprises alloys between the first and second metals and/or ternary carbides comprising the first and second metals.

In an embodiment, the activated catalyst comprises CoSn alloys and/or $Co_3SnC_x$, wherein x lies in the range from 0.7 to 1.0, on the surface of the catalyst.

In an embodiment, the support is chosen between the following: alumina, a spinel of alumina, a high temperature stable catalyst carrier in the form of an oxide a carbide or a nitride. As an example, the spinel of alumina may be $ZnAl_2O_4$ or $MgAl_2O_4$, and the oxide could e.g. be $CeO_2$ or $ZrO_2$.

Another aspect of the invention relates to a method for activating a catalyst, comprising the steps of:
providing a non-activated catalyst,
passing a feed stream comprising ammonia and methanol over the non-activated catalyst for at least 1 hour at a temperature of between about 400° C. and about 700° C. at a space velocity of at least 1000 $h^{-1}$.

Prior to activating the catalyst, it may be reduced in a reducing atmosphere, e.g. by passing 10 vol % $H_2$ in $N_2$ over a non-reduced (and non-activated) catalyst for 4 hours at a space velocity of 16000 $h^{-1}$ at a temperature of between about 500° C. and about 800° C.

A further aspect of the invention relates to the use of a catalyst according to the invention for catalysing reactions producing a product gas comprising acetonitrile and/or hydrogen cyanide from ammonia and methanol.

The following is a detailed description of experiments. The depicted in the accompanying drawings. The embodiments are examples and are in such detail as to clearly communicate the invention. However, the amount of detail offered is not intended to limit the anticipated variations of embodiments; but on the contrary, the intention is to cover all modifications, equivalents, and alternatives falling within the spirit and scope of the present invention as defined by the appended claims.

EXPERIMENT 1

Table 1 below show data of experimental data. Table 1 shows a product gas composition at four different reaction temperatures.

TABLE 1

10% Co-24% $Sn/Al_2O_3$

| | | | | Inlet | | Outlet | | | Dimethyl- |
|---|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | ether [vol %] |
| 1 | 0.4 | 400.2 | 100.3 | 9.93 | 9.01 | 1.70 | 0.15 | 0.23 | 2.31 |
| 2 | 0.8 | 400.0 | 100.3 | 9.93 | 9.01 | 1.69 | 0.16 | 0.21 | 2.38 |
| 3 | 1.3 | 400.3 | 100.3 | 9.93 | 9.01 | 1.86 | 0.16 | 0.20 | 2.61 |
| 4 | 1.7 | 400.3 | 100.4 | 9.92 | 9.01 | 1.87 | 0.16 | 0.19 | 2.74 |
| 5 | 2.2 | 400.0 | 100.3 | 9.93 | 9.01 | 1.91 | 0.16 | 0.18 | 2.79 |
| 6 | 3.0 | 450.6 | 100.3 | 9.93 | 9.01 | 1.08 | 0.78 | 1.14 | 1.00 |
| 7 | 3.4 | 450.1 | 100.3 | 9.93 | 9.01 | 0.78 | 0.81 | 1.05 | 0.83 |
| 8 | 3.9 | 450.2 | 100.3 | 9.93 | 9.01 | 0.82 | 0.81 | 0.97 | 1.10 |

TABLE 1-continued

10% Co-24% Sn/Al$_2$O$_3$

| | | | Inlet | | Outlet | | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 9 | 4.3 | 450.0 | 100.3 | 9.93 | 9.01 | 0.83 | 0.81 | 0.94 | 1.03 |
| 10 | 4.8 | 450.1 | 100.3 | 9.93 | 9.01 | 0.82 | 0.81 | 0.89 | 1.07 |
| 11 | 5.4 | 500.2 | 100.3 | 9.93 | 9.01 | 0.06 | 1.11 | 2.76 | 0.03 |
| 12 | 5.9 | 500.3 | 100.3 | 9.93 | 9.01 | 0.08 | 1.19 | 2.77 | 0.05 |
| 13 | 6.3 | 499.9 | 100.4 | 9.92 | 9.01 | 0.11 | 1.27 | 2.70 | 0.08 |
| 14 | 14.2 | 550.3 | 100.3 | 9.93 | 9.01 | 0 | 0.74 | 3.34 | 0 |
| 15 | 14.7 | 549.8 | 100.3 | 9.93 | 9.01 | 0 | 0.78 | 3.43 | 0 |
| 16 | 15.1 | 549.9 | 100.4 | 9.92 | 9.01 | 0 | 0.79 | 3.43 | 0 |

The catalyst used in EXPERIMENT 1 of Table 1 was 600 mg of a catalyst which prior to activation comprised 10 wt % Co, 24 wt % Sn on a Al$_2$O$_3$ carrier. In all experiments, the feed stream comprised 9.9 vol % CH$_3$OH (MeOH) and 9.0 vol % NH$_3$ (ammonia) in N$_2$. From Table 1 it is seen that acetonitrile is present in the outlet gas or product gas at temperatures of 400° C. and 450° C., however only at a comparatively low percentage of the product gas, but that at process temperatures of 500° C. and 550° C. the percentage of acetonitrile in the outlet gas is increased considerably. It is also seen that at 550° C., there is no methanol or dimethyl ether in the product gas, and that the amount of methanol and dimethyl ether at 550° C. is rather low. At 500° C. and 550° C., the main product is acetonitrile, and the methanol conversion is complete. Thus, the process and catalyst of the invention operates to form a C$_2$ species from a C$_1$ species.

EXPERIMENT 2

Table 2 shows data of further experiments. Table 2 shows data of product gas composition for different ratios between methanol and ammonia, and for different flow rates.

The catalyst used in the Experiment 2 shown in Table 2 was 600 mg of a catalyst which prior to activation comprised 10 wt % Co, 24 wt % Sn on a Al$_2$O$_3$ carrier. In the first three tests of Experiment 2, the feed stream comprised 9.9 vol % CH$_3$OH (MeOH) and 9.0 vol % NH$_3$ (ammonia) in N$_2$, i.e. a ratio CH$_3$OH:NH$_3$ ratio of 1.1:1; in the subsequent nine tests of Experiment 2, the feed stream comprised 16.5 vol % CH$_3$OH (MeOH) and 8.4 vol % NH$_3$ (ammonia) in N$_2$, i.e. a ratio CH$_3$OH:NH$_3$ ratio of 2.0:1.

From Table 2 it is seen that acetonitrile is the main constituents out of methanol (MeOH, CH$_3$OH), hydrogen cyanide (HCN), acetonitrile (CH$_3$CH) and dimethyl ether in the outlet gas or product gas.

It is also seen that at increasing the ratio CH$_3$OH:NH$_3$ from about 1:1 to 2:1 provides a higher amount of hydrogen cyanide, dimethyl ether and methanol in the product gas, when the flow is unchanged. However, when the flow is reduced by half, the amounts of hydrogen cyanide, dimethyl ether and methanol in the product gas is reduced.

Again, Experiment 2 shows that the process and catalyst of the invention operates to form a C$_2$ species from a C$_1$ species.

TABLE 2

10% Co-24% Sn/Al$_2$O$_3$

| | | | Inlet | | Outlet | | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 5.4 | 500.2 | 100.3 | 9.93 | 9.01 | 0.06 | 1.11 | 2.76 | 0.03 |
| 2 | 5.9 | 500.3 | 100.3 | 9.93 | 9.01 | 0.08 | 1.19 | 2.77 | 0.05 |
| 3 | 6.3 | 499.9 | 100.4 | 9.92 | 9.01 | 0.11 | 1.27 | 2.70 | 0.08 |
| 4 | 6.8 | 499.9 | 100.5 | 16.52 | 8.35 | 0.70 | 1.50 | 2.73 | 1.02 |
| 5 | 7.2 | 500.0 | 100.5 | 16.52 | 8.35 | 0.81 | 1.48 | 2.51 | 1.31 |
| 6 | 7.7 | 500.2 | 100.4 | 16.53 | 8.35 | 0.70 | 1.50 | 2.55 | 0.80 |
| 7 | 8.1 | 500.0 | 50.5 | 16.43 | 8.36 | 0.40 | 1.24 | 3.15 | 0.38 |
| 8 | 8.6 | 499.7 | 50.5 | 16.43 | 8.36 | 0.28 | 1.09 | 3.25 | 0.21 |
| 9 | 9.0 | 500.2 | 50.5 | 16.43 | 8.36 | 0.29 | 1.10 | 3.24 | 0.22 |
| 10 | 9.8 | 550.8 | 50.5 | 16.43 | 8.36 | 0 | 0.20 | 4.39 | 0 |
| 11 | 10.3 | 550.2 | 50.5 | 16.43 | 8.36 | 0 | 0.20 | 4.36 | 0 |
| 12 | 10.7 | 550.2 | 50.5 | 16.43 | 8.36 | 0 | 0.22 | 4.39 | 0 |

EXPERIMENT 3

Table 3 shows data of further experiments. Table 3 shows data of product gas composition for different ratios between methanol and ammonia, and for different flow rates.

TABLE 3

10% Fe-24% Sn/Al$_2$O$_3$

| | | | Inlet | | | Outlet | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 0.4 | 399.6 | 100.4 | 9.97 | 9.00 | 8.39 | 0.46 | 0.00 | 0.21 |
| 2 | 0.9 | 399.7 | 100.4 | 9.97 | 9.00 | 8.14 | 0.47 | 0.00 | 0.22 |
| 3 | 1.3 | 400.4 | 100.4 | 9.97 | 9.00 | 8.09 | 0.50 | 0.00 | 0.21 |
| 4 | 1.8 | 400.3 | 100.3 | 9.97 | 9.00 | 7.92 | 0.50 | 0.00 | 0.21 |
| 5 | 2.2 | 453.7 | 100.4 | 9.97 | 9.00 | 1.24 | 1.74 | 0.26 | 0.42 |
| 6 | 2.7 | 450.6 | 100.4 | 9.97 | 9.00 | 1.80 | 1.78 | 0.23 | 0.44 |
| 7 | 3.1 | 449.4 | 100.4 | 9.97 | 9.00 | 1.89 | 1.77 | 0.23 | 0.45 |
| 8 | 3.5 | 449.8 | 100.4 | 9.97 | 9.00 | 1.92 | 1.75 | 0.22 | 0.45 |
| 9 | 4.0 | 504.0 | 100.4 | 9.97 | 9.00 | 0.00 | 1.59 | 0.38 | 0.42 |
| 10 | 4.4 | 500.8 | 100.4 | 9.97 | 9.00 | 0.00 | 1.89 | 0.35 | 0.46 |
| 11 | 4.9 | 500.6 | 100.4 | 9.97 | 9.00 | 0.00 | 2.02 | 0.34 | 0.47 |
| 12 | 5.3 | 499.7 | 100.4 | 9.97 | 9.00 | 0.00 | 2.08 | 0.33 | 0.47 |
| 13 | 5.8 | 499.6 | 100.3 | 4.98 | 9.50 | 0.00 | 1.69 | 0.00 | 0.22 |
| 14 | 6.2 | 499.9 | 100.3 | 4.98 | 9.50 | 0.00 | 1.68 | 0.00 | 0.22 |
| 15 | 6.7 | 499.8 | 100.3 | 4.98 | 9.50 | 0.00 | 1.67 | 0.00 | 0.22 |
| 16 | 7.1 | 499.6 | 150.2 | 5.00 | 9.50 | 0.00 | 1.81 | 0.00 | 0.21 |
| 17 | 7.6 | 499.5 | 150.2 | 5.00 | 9.50 | 0.00 | 1.81 | 0.00 | 0.21 |
| 18 | 8.0 | 500.4 | 150.2 | 5.00 | 9.50 | 0.00 | 1.81 | 0.00 | 0.20 |
| 19 | 8.4 | 400.5 | 100.4 | 9.97 | 9.00 | 8.21 | 0.30 | 0.00 | 0.21 |
| 20 | 8.9 | 399.6 | 100.4 | 9.97 | 9.00 | 8.14 | 0.28 | 0.00 | 0.21 |
| 21 | 9.3 | 400.2 | 100.4 | 9.97 | 9.00 | 8.30 | 0.28 | 0.00 | 0.23 |
| 22 | 9.8 | 452.1 | 100.4 | 9.97 | 9.00 | 2.35 | 1.56 | 0.24 | 0.44 |
| 23 | 10.2 | 450.6 | 100.4 | 9.97 | 9.00 | 2.98 | 1.54 | 0.22 | 0.44 |
| 24 | 10.7 | 450.4 | 100.4 | 9.97 | 9.00 | 2.93 | 1.53 | 0.21 | 0.44 |
| 25 | 11.1 | 450.1 | 100.4 | 9.97 | 9.00 | 3.03 | 1.52 | 0.21 | 0.44 |

The catalyst used in the Experiment 3 shown in Table 3 was 600 mg of a catalyst which prior to activation comprised 10 wt % Fe, 24 wt % Sn on a Al$_2$O$_3$ carrier.

In the tests numbered 1-12 and the tests numbered 19-25 of Experiment 3, the feed stream comprised 10.0 vol % CH$_3$OH (MeOH) and 9.0 vol % NH$_3$ (ammonia) in N$_2$, i.e. a ratio CH$_3$OH:NH$_3$ ratio of 1.1:1; in the tests 14-18 of Experiment 3, the feed stream comprised 5.0 vol % CH$_3$OH (MeOH) and 9.54 vol % NH$_3$ (ammonia) in N$_2$, i.e. a ratio CH$_3$OH:NH$_3$ ratio of 1:1.9.

From Table 3 it is seen that hydrogen cyanide is the main product out of hydrogen cyanide (HCN), acetonitrile (CH3CH) and dimethyl ether (DME) at 450° C. and above.

It is also seen that increasing the ratio CH3OH:NH3 from about 1:1 to 1:1.9 results in a decrease in the HCN production and a halving of the DME production. The product gas contains no acetonitrile at this ratio.

Increasing the flow rate from 100 to 150 Nml/min results in an increase of HCN in the product gas.

EXPERIMENT 4

Table 4 shows data of further experiments. Table 4 shows data of product gas composition for different ratios between methanol and ammonia, and for different flow rates.

TABLE 4

10% Fe-12% Zn/Al$_2$O$_3$

| | | | Inlet | | | Outlet | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 0.4 | 400.0 | 100.3 | 9.97 | 9.00 | 0.00 | 0.11 | 1.14 | 0.28 |
| 2 | 0.8 | 400.3 | 100.3 | 9.97 | 9.00 | 0.00 | 0.11 | 1.09 | 0.36 |
| 3 | 1.3 | 400.2 | 100.4 | 9.97 | 9.00 | 0.00 | 0.11 | 1.10 | 0.36 |
| 4 | 1.7 | 400.3 | 150.2 | 9.99 | 9.00 | 0.00 | 0.09 | 0.81 | 0.92 |
| 5 | 2.1 | 400.1 | 150.2 | 9.99 | 9.00 | 0.00 | 0.09 | 0.85 | 0.89 |
| 6 | 2.6 | 400.4 | 150.2 | 9.99 | 9.00 | 0.00 | 0.09 | 0.85 | 0.85 |
| 7 | 2.9 | 400.2 | 100.4 | 16.54 | 8.35 | 1.26 | 0.00 | 0.51 | 2.95 |
| 8 | 3.3 | 400.8 | 100.4 | 16.54 | 8.35 | 1.16 | 0.00 | 0.51 | 2.91 |

TABLE 4-continued

10% Fe-12% Zn/Al$_2$O$_3$

|   | | Inlet | | | Outlet | | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 9 | 3.8 | 400.4 | 100.4 | 16.54 | 8.35 | 1.14 | 0.00 | 0.50 | 2.95 |
| 10 | 4.2 | 454.2 | 100.4 | 16.54 | 8.35 | 0.00 | 0.57 | 2.44 | 0.00 |
| 11 | 4.6 | 450.6 | 100.4 | 16.54 | 8.35 | 0.00 | 0.48 | 2.36 | 0.00 |
| 12 | 5.1 | 450.3 | 100.5 | 16.53 | 8.35 | 0.00 | 0.44 | 2.32 | 0.03 |
| 13 | 5.5 | 450.5 | 100.4 | 16.54 | 8.35 | 0.00 | 0.39 | 2.31 | 0.04 |
| 14 | 6.0 | 450.1 | 100.3 | 9.97 | 9.00 | 0.00 | 0.41 | 1.70 | 0.00 |
| 15 | 6.4 | 450.2 | 100.4 | 9.97 | 9.00 | 0.00 | 0.42 | 1.71 | 0.00 |
| 16 | 6.8 | 449.9 | 100.3 | 9.97 | 9.00 | 0.00 | 0.43 | 1.69 | 0.00 |
| 17 | 7.3 | 450.0 | 100.3 | 4.98 | 9.50 | 0.00 | 0.18 | 1.11 | 0.00 |
| 18 | 7.7 | 450.1 | 100.3 | 4.98 | 9.50 | 0.00 | 0.20 | 1.15 | 0.00 |
| 19 | 8.2 | 450.3 | 100.3 | 4.98 | 9.50 | 0.00 | 0.20 | 1.14 | 0.00 |

The catalyst used in the Experiment 4 shown in Table 4 was 600 mg of a catalyst which prior to activation comprised 10 wt % Fe, 12 wt % Zn on a Al$_2$O$_3$ carrier.

In the tests 1-6 of Experiment 4, the feed stream comprised 10.0 vol % CH$_3$OH (MeOH) and 9.0 vol % NH$_3$ (ammonia) in N$_2$, i.e. a ratio CH$_3$OH:NH$_3$ ratio of 1.1:1; in the tests 7-13 of Experiment 4, the feed stream comprised 16.54 vol % CH$_3$OH (MeOH) and 8.35 vol % NH$_3$ (ammonia) in N$_2$, i.e. a ratio CH$_3$OH:NH$_3$ ratio of 1:2.0. The subsequent three test were with a feed stream comprising 10.0 vol % CH$_3$OH (MeOH) and 9.0 vol % NH$_3$ (ammonia) in N$_2$, i.e. a ratio CH$_3$OH:NH$_3$ ratio of 1.1:1, and the last three tests of Experiment 4 were with a feed stream comprising 5.0 vol % CH$_3$OH (MeOH) and 9.5 vol % NH$_3$ (ammonia) in N$_2$, i.e. a ratio CH$_3$OH:NH$_3$ ratio of 1:1.9.

From Table 4 it is seen that acetonitrile and hydrogen cyanide are present in the product gas in all tests, except from the three tests where the temperature is 400° C. and the ratio between methanol and ammonia in the feed stream is 1:2.0. In those three test, no HCN is present in the product gas.

EXPERIMENT 5

Table 5 shows data of further experiments, with a catalyst comprising Ni and Sn on a Al$_2$O$_3$. Table 5 shows data of product gas composition for different ratios between methanol and ammonia, and for different flow rates.

TABLE 5

10% Ni-24% Sn/Al$_2$O$_3$

|   | | Inlet | | | Outlet | | | |
|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 0.3 | 400.3 | 100.4 | 9.97 | 9.00 | 1.88 | 0.14 | 0.37 | 2.54 |
| 2 | 0.8 | 400.3 | 100.4 | 9.97 | 9.00 | 1.90 | 0.13 | 0.31 | 2.65 |
| 3 | 1.2 | 399.9 | 100.4 | 9.97 | 9.00 | 1.89 | 0.12 | 0.28 | 2.65 |
| 4 | 1.7 | 453.4 | 100.4 | 9.97 | 9.00 | 0.95 | 0.23 | 1.44 | 0.65 |
| 5 | 2.1 | 450.0 | 100.4 | 9.97 | 9.00 | 1.13 | 0.19 | 1.22 | 0.87 |
| 6 | 2.6 | 450.1 | 100.4 | 9.97 | 9.00 | 1.19 | 0.17 | 1.14 | 0.94 |
| 7 | 3.0 | 450.1 | 100.4 | 9.97 | 9.00 | 1.23 | 0.17 | 1.07 | 1.00 |
| 8 | 3.5 | 450.1 | 100.4 | 9.97 | 9.00 | 1.29 | 0.15 | 1.01 | 1.04 |
| 9 | 3.9 | 503.2 | 100.4 | 9.97 | 9.00 | 0.00 | 0.56 | 2.27 | 0.00 |
| 10 | 4.4 | 500.4 | 100.4 | 9.97 | 9.00 | 0.00 | 0.59 | 2.17 | 0.00 |
| 11 | 4.8 | 499.9 | 100.4 | 9.97 | 9.00 | 0.00 | 0.60 | 2.11 | 0.00 |
| 12 | 5.2 | 499.9 | 100.4 | 9.97 | 9.00 | 0.00 | 0.62 | 2.05 | 0.01 |
| 13 | 5.7 | 553.4 | 100.4 | 9.97 | 9.00 | 0.00 | 0.38 | 2.84 | 0.00 |
| 14 | 6.1 | 550.3 | 100.4 | 9.97 | 9.00 | 0.00 | 0.48 | 2.71 | 0.00 |
| 15 | 6.6 | 549.9 | 100.4 | 9.97 | 9.00 | 0.00 | 0.54 | 2.68 | 0.00 |
| 16 | 7.0 | 550.0 | 100.4 | 9.97 | 9.00 | 0.00 | 0.55 | 2.66 | 0.00 |
| 17 | 8.1 | 550.1 | 100.3 | 4.98 | 9.50 | 0.00 | 0.24 | 1.53 | 0.00 |
| 18 | 8.5 | 549.9 | 100.3 | 4.98 | 9.50 | 0.00 | 0.24 | 1.63 | 0.00 |
| 19 | 8.9 | 549.9 | 100.3 | 4.98 | 9.50 | 0.00 | 0.24 | 1.69 | 0.00 |
| 20 | 9.4 | 550.0 | 100.5 | 16.53 | 8.35 | 0.00 | 0.35 | 3.79 | 0.00 |
| 21 | 9.8 | 550.0 | 100.5 | 16.53 | 8.35 | 0.00 | 0.47 | 3.83 | 0.00 |
| 22 | 10.3 | 550.1 | 100.5 | 16.53 | 8.35 | 0.00 | 0.52 | 3.93 | 0.00 |
| 23 | 10.7 | 600.2 | 100.4 | 9.97 | 9.00 | 0.00 | 0.40 | 1.65 | 0.00 |
| 24 | 11.2 | 600.1 | 100.4 | 9.97 | 9.00 | 0.00 | 0.40 | 1.69 | 0.00 |
| 25 | 11.6 | 600.2 | 100.4 | 9.97 | 9.00 | 0.00 | 0.41 | 1.64 | 0.00 |

In tests 1-16 and 23-25 of Experiment 5, the feed stream comprised 10.0 vol % $CH_3OH$ (MeOH) and 9.0 vol % $NH_3$ (ammonia) in $N_2$, i.e. a ratio $CH_3OH:NH_3$ ratio of 1.1:1; in the tests 17-19 of Experiment 5, the feed stream comprised 5.0 vol % $CH_3OH$ (MeOH) and 9.5 vol % $NH_3$ (ammonia) in $N_2$, i.e. a ratio $CH_3OH:NH_3$ ratio of 1:1.9. In the tests 20-22 the feed stream comprised 16.54 vol % $CH_3OH$ (MeOH) and 8.35 vol % $NH_3$ (ammonia) in $N_2$, i.e. a ratio $CH_3OH:NH_3$ ratio of 1:2.0.

It is seen from Table 5, that also a Ni—Sn catalyst on a $Al_2O_3$ carrier is effective in catalyzing the conversion of ammonia and methanol to hydrogen cyanide and acetonitrile. At temperatures of 500° C. and above, the conversion of methanol is complete.

EXPERIMENT 6

Table 6 shows data on further experiments with a catalyst comprising Fe and Sn on a $Al_2O_3$ support. Table 6 shows data of product gas composition for different ratios between methanol and ammonia, and for different flow rates.

TABLE 6

10% Fe-24% $Sn/Al_2O_3$

| # | Time [h] | Temp. [° C.] | Total flow [Nml/min] | Inlet MeOH [vol %] | Inlet NH3 [vol %] | Outlet MeOH [vol %] | Outlet HCN [vol %] | Outlet Acetonitrile [vol %] | Outlet Dimethyl-ether [vol %] |
|---|---|---|---|---|---|---|---|---|---|
| 1 | 0.4 | 450.1 | 100.3 | 5.0 | 9.5 | 0.00 | 1.60 | 0.00 | 0.48 |
| 2 | 0.9 | 449.9 | 100.3 | 5.0 | 9.5 | 0.00 | 1.62 | 0.30 | 0.49 |
| 3 | 1.3 | 450.2 | 100.3 | 5.0 | 9.5 | 0.00 | 1.62 | 0.30 | 0.52 |
| 4 | 1.8 | 499.7 | 100.3 | 5.0 | 9.5 | 0.00 | 1.28 | 0.55 | 0.16 |
| 5 | 2.2 | 500.9 | 100.3 | 5.0 | 9.5 | 0.00 | 1.44 | 0.57 | 0.21 |
| 6 | 2.7 | 500.2 | 100.3 | 5.0 | 9.5 | 0.00 | 1.44 | 0.55 | 0.23 |
| 7 | 3.1 | 499.9 | 100.3 | 5.0 | 9.5 | 0.00 | 1.47 | 0.56 | 0.25 |
| 8 | 3.7 | 539.1 | 100.3 | 5.0 | 9.5 | 0.00 | 0.67 | 0.63 | 0.01 |
| 9 | 4.1 | 550.9 | 100.3 | 5.0 | 9.5 | 0.00 | 0.82 | 0.69 | 0.01 |
| 10 | 4.6 | 549.9 | 100.3 | 5.0 | 9.5 | 0.00 | 0.90 | 0.65 | 0.01 |
| 11 | 5.0 | 550.1 | 100.3 | 5.0 | 9.5 | 0.00 | 0.94 | 0.63 | 0.01 |
| 12 | 5.4 | 449.9 | 150.3 | 5.0 | 9.5 | 0.00 | 1.45 | 0.00 | 0.44 |
| 13 | 5.8 | 450.1 | 150.3 | 5.0 | 9.5 | 0.00 | 1.46 | 0.21 | 0.45 |
| 14 | 6.3 | 450.2 | 150.3 | 5.0 | 9.5 | 0.00 | 1.43 | 0.20 | 0.45 |
| 15 | 7.4 | 450.1 | 50.5 | 4.9 | 9.5 | 0.00 | 1.10 | 0.00 | 0.35 |
| 16 | 7.8 | 449.9 | 50.5 | 5.0 | 9.5 | 0.00 | 1.30 | 0.36 | 0.52 |
| 17 | 8.3 | 450.1 | 50.5 | 5.0 | 9.5 | 0.00 | 1.32 | 0.37 | 0.55 |
| 18 | 8.7 | 503.7 | 150.3 | 5.0 | 9.5 | 0.00 | 1.70 | 0.00 | 0.25 |
| 19 | 9.1 | 500.4 | 150.3 | 5.0 | 9.5 | 0.00 | 1.78 | 0.00 | 0.28 |
| 20 | 9.6 | 500.2 | 150.3 | 5.0 | 9.5 | 0.00 | 1.74 | 0.00 | 0.27 |
| 21 | 10.0 | 500.0 | 150.3 | 5.0 | 9.5 | 0.00 | 1.84 | 0.00 | 0.25 |
| 22 | 10.5 | 500.2 | 50.5 | 4.9 | 9.5 | 0.00 | 1.45 | 0.65 | 0.13 |
| 23 | 10.9 | 499.8 | 50.5 | 4.9 | 9.5 | 0.00 | 1.28 | 0.55 | 0.07 |
| 24 | 11.4 | 500.0 | 50.5 | 5.0 | 9.5 | 0.00 | 1.26 | 0.51 | 0.06 |
| 25 | 11.5 | 449.4 | 100.3 | 13.1 | 8.7 | 3.87 | 1.85 | 0.38 | 0.84 |
| 26 | 11.9 | 450.3 | 100.3 | 13.1 | 8.7 | 3.56 | 1.75 | 0.37 | 0.91 |
| 27 | 12.4 | 450.3 | 100.3 | 13.1 | 8.7 | 3.64 | 1.68 | 0.36 | 0.92 |
| 28 | 12.8 | 495.8 | 100.3 | 13.1 | 8.7 | 0.00 | 2.45 | 0.63 | 0.51 |
| 29 | 13.3 | 500.4 | 100.3 | 13.1 | 8.7 | 0.00 | 2.53 | 0.60 | 0.55 |
| 30 | 13.7 | 500.2 | 100.3 | 13.1 | 8.7 | 0.00 | 2.55 | 0.59 | 0.57 |
| 31 | 14.2 | 500.1 | 100.3 | 13.1 | 8.7 | 0.00 | 2.53 | 0.57 | 0.54 |
| 32 | 15.1 | 450.1 | 50.6 | 13.0 | 8.7 | 1.48 | 1.83 | 0.51 | 1.01 |
| 33 | 15.5 | 449.9 | 50.6 | 13.0 | 8.7 | 1.63 | 1.78 | 0.51 | 1.08 |
| 34 | 16.0 | 449.9 | 50.6 | 13.0 | 8.7 | 1.57 | 1.78 | 0.51 | 1.08 |
| 35 | 16.4 | 450.0 | 150.3 | 13.1 | 8.7 | 7.35 | 1.48 | 0.29 | 0.49 |
| 36 | 16.8 | 449.9 | 150.3 | 13.1 | 8.7 | 7.15 | 1.24 | 0.29 | 0.63 |
| 37 | 17.3 | 450.0 | 150.3 | 13.1 | 8.7 | 7.19 | 1.20 | 0.28 | 0.65 |
| 38 | 17.7 | 449.9 | 150.3 | 13.1 | 8.7 | 7.19 | 1.19 | 0.29 | 0.65 |
| 39 | 19.2 | 500.1 | 150.3 | 13.1 | 8.7 | 0.00 | 2.93 | 0.47 | 0.53 |
| 40 | 19.7 | 500.1 | 150.3 | 13.1 | 8.7 | 0.00 | 2.98 | 0.46 | 0.57 |
| 41 | 20.1 | 499.8 | 150.3 | 13.1 | 8.7 | 0.00 | 2.96 | 0.46 | 0.56 |
| 42 | 20.6 | 500.2 | 50.6 | 13.0 | 8.7 | 0.00 | 2.10 | 0.59 | 0.32 |
| 43 | 21.0 | 500.1 | 50.6 | 13.0 | 8.7 | 0.00 | 2.06 | 0.59 | 0.27 |
| 44 | 21.5 | 499.9 | 50.6 | 13.0 | 8.7 | 0.00 | 2.15 | 0.56 | 0.30 |
| 45 | 21.9 | 499.8 | 100.3 | 5.0 | 9.5 | 0.00 | 1.91 | 0.26 | 0.14 |
| 46 | 22.3 | 500.0 | 100.3 | 5.0 | 9.5 | 0.00 | 1.90 | 0.26 | 0.13 |
| 47 | 22.8 | 500.0 | 100.3 | 5.0 | 9.5 | 0.00 | 1.89 | 0.24 | 0.13 |

It is seen from Table 6, that also a Fe—Sn catalyst on a Al$_2$O$_3$ carrier is effective in catalyzing the conversion of ammonia and methanol to hydrogen cyanide and acetonitrile.

EXPERIMENT 7

Table 7 shows data on further experiments with a catalyst comprising Co and Sn on a Al$_2$O$_3$ support. Table 7 shows data of product gas composition for different ratios between methanol and ammonia, and for different flow rates.

methanol and 9.5 vol % ammonia in nitrogen (corresponding to a CH$_3$OH:NH$_3$ ratio of 0.53:1) was used. When the CH$_3$OH:NH$_3$ ratio is decreased to 0.53:1, both the hydrogen cyanide and the acetonitrile concentrations decrease; however, the selectivity towards the two increases. When the total inlet flow is lowered to 50 Nml/min, the production of acetonitrile increases while the hydrogen cyanide concentration decreases accordingly.

TABLE 7

10% Co-24% Sn/Al$_2$O$_3$

| | | | | Inlet | | Outlet | | | |
|---|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 0.4 | 450.1 | 100.3978 | 10.0 | 9.0 | 1.22 | 0.47 | 0.9 | 1.4 |
| 2 | 0.8 | 450.1 | 100.3978 | 10.0 | 9.0 | 1.32 | 0.44 | 0.8 | 1.6 |
| 3 | 1.3 | 450.1 | 100.3978 | 10.0 | 9.0 | 1.40 | 0.41 | 0.8 | 1.7 |
| 4 | 1.7 | 503.6 | 100.401 | 10.0 | 9.0 | 0.00 | 0.61 | 2.2 | 0.0 |
| 5 | 2.2 | 500.4 | 100.3849 | 10.0 | 9.0 | 0.00 | 0.70 | 2.1 | 0.0 |
| 6 | 2.6 | 499.9 | 100.3978 | 10.0 | 9.0 | 0.00 | 0.72 | 2.1 | 0.0 |
| 7 | 3.1 | 500.1 | 100.3978 | 10.0 | 9.0 | 0.00 | 0.77 | 2.1 | 0.0 |
| 8 | 3.5 | 499.8 | 100.3267 | 5.0 | 9.5 | 0.00 | 0.49 | 1.5 | 0.0 |
| 9 | 4.0 | 499.7 | 100.3363 | 5.0 | 9.5 | 0.00 | 0.51 | 1.5 | 0.0 |
| 10 | 4.4 | 500.0 | 100.3267 | 5.0 | 9.5 | 0.00 | 0.52 | 1.4 | 0.0 |
| 11 | 5.0 | 499.9 | 50.48469 | 5.0 | 9.5 | 0.00 | 0.17 | 1.7 | 0.0 |
| 12 | 5.5 | 499.8 | 50.49114 | 4.9 | 9.5 | 0.00 | 0.24 | 1.7 | 0.0 |
| 13 | 5.9 | 499.9 | 50.48469 | 5.0 | 9.5 | 0.00 | 0.25 | 1.6 | 0.0 |
| 14 | 6.6 | 500.1 | 50.48469 | 5.0 | 9.5 | 0.00 | 0.29 | 0.0 | 0.0 |
| 15 | 7.1 | 499.9 | 150.2778 | 5.0 | 9.5 | 0.00 | 0.92 | 1.3 | 0.0 |
| 16 | 7.5 | 499.9 | 150.2778 | 5.0 | 9.5 | 0.00 | 0.91 | 1.3 | 0.0 |
| 17 | 8.0 | 500.2 | 150.2778 | 5.0 | 9.5 | 0.00 | 0.86 | 1.2 | 0.0 |

It is seen from Table 7, that also a Co—Sn catalyst on a Al$_2$O$_3$ carrier is effective in catalyzing the conversion of ammonia and methanol to hydrogen cyanide and acetonitrile. A total flow of 50-150 Nml/min containing either 10.0 vol % methanol and 9.0 vol % ammonia in nitrogen (corresponding to a CH$_3$OH:NH$_3$ ratio of 1.11:1) or 5.0 vol %

EXPERIMENT 8

Table 8 shows data on further experiments with a catalyst comprising Co and Sn on Al$_2$O$_3$ support. Table 8 shows data of product gas composition for different ratios between methanol and ammonia, and for different flow rates.

TABLE 8

10% Co-24% Sn/Al$_2$O$_3$

| | | | | Inlet | | Outlet | | | |
|---|---|---|---|---|---|---|---|---|---|
| # | Time [h] | Temp. [° C.] | Total flow [Nml/min] | MeOH [vol %] | NH3 [vol %] | MeOH [vol %] | HCN [vol %] | Acetonitrile [vol %] | Dimethyl-ether [vol %] |
| 1 | 0.4 | 399.6 | 100.6 | 9.9 | 9.0 | 3.51 | 0.38 | 0.00 | 2.40 |
| 2 | 0.9 | 399.8 | 100.6 | 9.9 | 9.0 | 3.70 | 0.40 | 0.00 | 2.43 |
| 3 | 1.4 | 400.3 | 100.6 | 9.9 | 9.0 | 3.78 | 0.39 | 0.00 | 2.40 |
| 4 | 1.8 | 453.2 | 100.6 | 9.9 | 9.0 | 0.00 | 0.73 | 0.86 | 1.66 |
| 5 | 2.3 | 450.3 | 100.6 | 9.9 | 9.0 | 0.00 | 0.71 | 0.82 | 1.86 |
| 6 | 2.8 | 449.9 | 100.6 | 9.9 | 9.0 | 0.00 | 0.66 | 0.76 | 1.99 |
| 7 | 3.2 | 450.1 | 100.6 | 9.9 | 9.0 | 0.00 | 0.60 | 0.65 | 2.13 |
| 8 | 3.7 | 503.7 | 100.6 | 9.9 | 9.0 | 0.00 | 1.22 | 1.77 | 0.31 |
| 9 | 4.2 | 500.1 | 100.6 | 9.9 | 9.0 | 0.00 | 1.19 | 1.59 | 0.52 |
| 10 | 4.6 | 500.1 | 100.6 | 9.9 | 9.0 | 0.00 | 1.20 | 1.47 | 0.60 |
| 11 | 5.1 | 499.7 | 102.7 | 9.7 | 8.8 | 0.00 | 1.18 | 1.43 | 0.66 |
| 12 | 6.2 | 549.7 | 100.6 | 10.0 | 9.0 | 0.00 | 0.74 | 2.42 | 0.00 |
| 13 | 6.6 | 548.5 | 100.5 | 10.0 | 9.0 | 0.00 | 0.99 | 2.45 | 0.00 |
| 14 | 7.1 | 550.3 | 100.6 | 9.9 | 9.0 | 0.00 | 1.17 | 2.45 | 0.00 |

It is again seen from Table 8, that a Co—Sn catalyst on a Al₂O₃ carrier is effective in catalyzing the conversion of ammonia and methanol to hydrogen cyanide and acetonitrile. In the experiment of Table 8, the carrier gas was argon. Therefore, it was possible to determine whether the direct decomposition of ammonia to nitrogen and hydrogen occurs over the catalyst. As no nitrogen was detected, this reaction does not appear to take place at the tested temperatures.

It should be noted that even though the feed stream of Experiments 1 to 8 comprised about 75 vol % to 80 vol % carrier gas, such as N₂ or argon, the invention is not limited to such a feed stream. It is conceivable that the feed stream comprises much more ammonia and methanol, e.g. that the feed stream essentially consists of ammonia and methanol.

Figure 1:
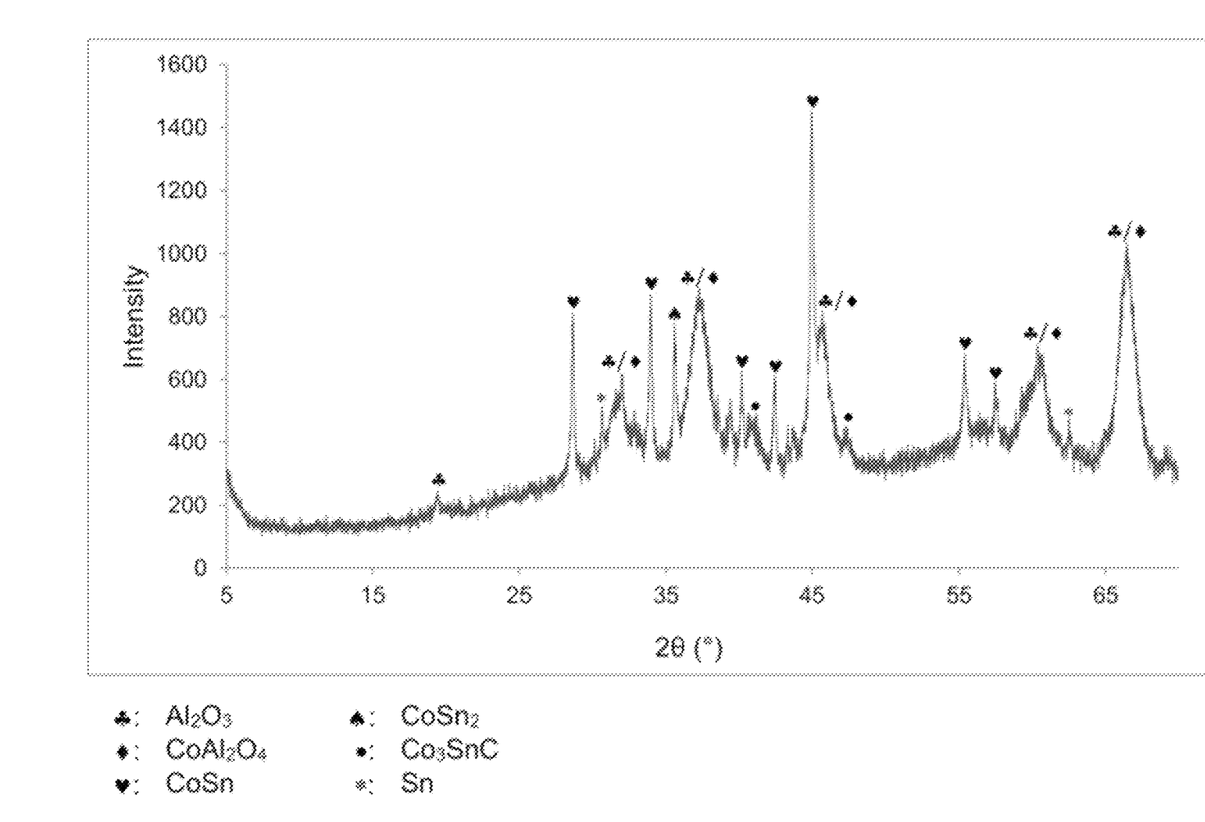
FIG. 1 is an XRD plot of activated catalyst according to the invention.

FIG. 1 is an XRD plot of an activated Co—Sn catalyst supported on Al₂O₃ according to the invention. In the XRD plot, intensity peaks corresponding to specific compounds have been identified, as indicated by the legend of FIG. 1 and in Table 9 below.

TABLE 9

|  | wt % | D (A) | a (A) | c (A) |
|---|---|---|---|---|
| Co₃SnC | 1.4 | 185 | 3.821 | |
| CoAl₂O₄ | 51 | 56 | 7.987 | |
| CoSn | 4.5 | 502 | 5.276 | 4.26 |
| CoSn₂ | 1 | 809 | 6.354 | 5.45 |
| gamma-Al₂O₃ | 42 | 122 | 7.933 | |
| Sn | 0.2 | 3837 | 5.825 | 3.18 |

In FIG. 1, the main phase is gamma-Al₂O₃ giving a high background. It is seen from Table 9 that the spent or activated catalyst comprises alloys between the Co and Sn, e.g. CoSn and CoSn₂, as well as a ternary carbide comprising the first and the second metals, in the form of Co₃SnC.

The term "ternary carbides" is meant to denote a carbide comprising the first and second metals; the plural form of the term is not meant to denote that different types of ternary carbides exist. Instead the plural form of the term "ternary carbides" indicate that more than one molecule of the carbide is comprised in the catalyst. Likewise, the term "alloys between the first and second metal" is not meant to indicate that more than one type of alloy is comprised in the catalyst, only that more than one alloy molecule is comprised within the catalyst.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicant's general inventive concept.

The invention claimed is:

1. A process comprising:
    producing a product gas comprising acetonitrile and/or hydrogen cyanide from a feed stream comprising ammonia and methanol over a solid catalyst at a pressure and a temperature,
    wherein the catalyst comprises a support, a first metal and a second metal on said support, wherein said first metal and said second metal are in the form of a chemical compound selected from the group consisting of an alloy consisting of the first metal and the second metal, a ternary carbide comprising the first metal and the second metal, and a mixture thereof, wherein said first metal is Fe, Ru, Ni or Co and said second metal is Sn, Zn, or Ge, wherein the catalyst comprises alloys between the first and second metals and/or ternary carbides comprising the first and the second metals,
    wherein the pressure is atmospheric pressure or higher and the temperature lies in a range from about 400° C. to about 700° C., and
    wherein the catalyst is capable of catalyzing the following reactions:
    1a) formation of formamide from methanol and ammonia;
    1b) decomposition of formamide to hydrogen cyanide; and
    2) cyanation of methanol to acetonitrile.

2. A process according to claim 1, where the temperature lies in a range from about 500° C. to about 600° C.

3. A process according to claim 1, wherein the support is chosen between the following: alumina, a spinel of alumina, and a high temperature stable catalyst carrier in the form of an oxide, a carbide, or a nitride.

4. A process according to claim 1, wherein further comprising controlling the ratio between acetonitrile and hydrogen cyanide in the product gas by controlling the ratio of ammonia and methanol in the feed stream and/or the process temperature.

5. A process according to claim 1, wherein said first metal and said second metal are in the form of an alloy of the first metal and the second metal.

6. A process according to claim 1, wherein said first metal and said second metal are in the form of an alloy consisting of the first metal and the second metal.

7. A process according to claim 1, wherein said first metal and said second metal are in the form of a ternary carbide comprising the first metal and the second metal.

* * * * *